United States Patent
Totsuka et al.

(10) Patent No.: US 11,857,155 B2
(45) Date of Patent: Jan. 2, 2024

(54) IMAGING APPARATUS, METHOD OF OPERATING IMAGING APPARATUS, AND RECORDING MEDIUM

(71) Applicant: OLYMPUS CORPORATION, Hachioji (JP)

(72) Inventors: Takuya Totsuka, Tokyo (JP); Kotaro Ogasawara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 727 days.

(21) Appl. No.: 17/068,966

(22) Filed: Oct. 13, 2020

(65) Prior Publication Data
US 2021/0029289 A1 Jan. 28, 2021

Related U.S. Application Data

(63) Continuation of application No. PCT/JP2018/016581, filed on Apr. 24, 2018.

(51) Int. Cl.
*A61B 1/00* (2006.01)
*A61B 1/06* (2006.01)
(Continued)

(52) U.S. Cl.
CPC ...... *A61B 1/00036* (2013.01); *A61B 1/00006* (2013.01); *A61B 1/00009* (2013.01);
(Continued)

(58) Field of Classification Search
CPC ........ H04N 7/18; H04N 23/555; H04N 23/56; H04N 23/651; H04N 23/667; H04N 23/71;
(Continued)

(56) References Cited

U.S. PATENT DOCUMENTS 9,182,337 B2 * 11/2015 Kamee .................. G01N 21/01
2022/0000336 A1 * 1/2022 Yanagihara ........ A61B 1/00016

FOREIGN PATENT DOCUMENTS

EP 2668889 A1 12/2013
EP 2695568 A1 2/2014
(Continued)

OTHER PUBLICATIONS

International Search Report dated Jun. 26, 2018, issued in counterpart application No. PCT/JP2018/016581, w/English translation (4 pages).

*Primary Examiner* — Lin Ye
*Assistant Examiner* — Chriss S Yoder, III
(74) *Attorney, Agent, or Firm* — WHDA, LLP

(57) ABSTRACT

An imaging apparatus includes a processor, an imaging device, and a light source. The processor is configured to determine whether or not the imaging device has gone out of space of which at least part is surrounded by an object when the imaging device is performing imaging after the imaging device is inserted into the space. The processor is configured to execute power-saving control when the processor determines that the imaging device has gone out of the space. In the power-saving control, the processor is configured to make power consumption of a control target less than power consumption of the control target before the power-saving control is executed. The control target is at least one of the imaging device and the light source.

11 Claims, 8 Drawing Sheets

(51) Int. Cl.
*G02B 7/36* (2021.01)
*G03B 13/36* (2021.01)
*H04N 23/71* (2023.01)
*H04N 23/74* (2023.01)
*H04N 23/50* (2023.01)
*G02B 23/24* (2006.01)

(52) U.S. Cl.
CPC .......... *A61B 1/0655* (2022.02); *A61B 1/0661* (2013.01); *G02B 7/36* (2013.01); *G02B 23/2484* (2013.01); *G03B 13/36* (2013.01); *H04N 23/71* (2023.01); *H04N 23/74* (2023.01); *A61B 1/00016* (2013.01); *A61B 1/00032* (2013.01); *H04N 23/555* (2023.01)

(58) Field of Classification Search
CPC ................ H04N 23/74; A61B 1/00006; A61B 1/00009; A61B 1/00016; A61B 1/00032; A61B 1/00036; A61B 1/045; A61B 1/0655; A61B 1/0661; G02B 7/36; G02B 23/2484; G03B 13/36
See application file for complete search history.

(56) References Cited

FOREIGN PATENT DOCUMENTS

| | | | |
|---|---|---|---|
| JP | 2002-253488 | A | 9/2002 |
| JP | 2005-073887 | A | 3/2005 |
| JP | 2005-080694 | A | 3/2005 |
| JP | 2011-147043 | A | 7/2011 |
| JP | 2012-152273 | A | 8/2012 |
| JP | 2012-217627 | A | 11/2012 |
| JP | 2013-094318 | A | 5/2013 |
| JP | 2014-027386 | A | 2/2014 |

\* cited by examiner

IMAGING APPARATUS, METHOD OF OPERATING IMAGING APPARATUS, AND RECORDING MEDIUM

BACKGROUND OF THE INVENTION

Field of the Invention

The present invention relates to an imaging apparatus, a method of operating the imaging apparatus, and a recording medium.

The present application is a continuation application based on International Patent Application No. PCT/JP2018/016581 filed on Apr. 24, 2018, the content of which is incorporated herein by reference.

Description of Related Art

Wireless endoscopes operating with batteries have been developed in recent years. As the battery capacity increases, the weight of a wireless endoscope increases. For this reason, portability is lost. Thus, it is desirable that a wireless endoscope does not waste power.

Japanese Unexamined Patent Application, First Publication No. 2013-094318 discloses technology of updating a correction table for correcting the battery residual capacity. In addition, Japanese Unexamined Patent Application, First Publication No. 2013-094318 suggests updating the correction table when equipment is idle.

SUMMARY OF THE INVENTION

According to a first aspect of the present invention, an imaging apparatus includes a processor, an imaging device configured to output image data, and a light source. The processor is configured to determine whether or not the imaging device has gone out of space of which at least part is surrounded by an object when the imaging device is performing imaging after the imaging device is inserted into the space. The processor is configured to execute power-saving control when the processor determines that the imaging device has gone out of the space. In the power-saving control, the processor is configured to make power consumption of a control target less than power consumption of the control target before the power-saving control is executed. The control target is at least one of the imaging device and the light source. The processor is configured to determine brightness on the basis of the image data. The processor is configured to reduce an amount of irradiation light of the light source when the brightness increases in a state in which the brightness is greater than or equal to a predetermined amount. The processor is configured to determine whether or not the brightness meets a first condition. The first condition represents that the brightness is continuously smaller than a first threshold value in a first period. The processor is configured to determine that the imaging device has gone out of the space when the brightness meets the first condition.

According to a second aspect of the present invention, in the first aspect, the processor may be configured to determine whether or not the imaging device has gone into the space while the processor executes the power-saving control. The processor may be configured to stop the power-saving control when the processor determines that the imaging device has gone into the space.

According to a third aspect of the present invention, in the second aspect, the processor may be configured to restrict the maximum amount of the irradiation light of the light source to less than or equal to a first light amount by executing the power-saving control. The processor may be configured to temporarily set the maximum amount to a second light amount greater than the first light amount after a second period elapses from a time point of starting the power-saving control. The processor may be configured to determine whether or not the brightness meets a second condition while the maximum amount is temporarily set to the second light amount. The second condition may represent that the brightness is continuously greater than a second threshold value in a third period. The processor may be configured to determine that the imaging device has gone into the space when the brightness meets the second condition.

According to a fourth aspect of the present invention, in the second aspect, the processor may be configured to restrict the maximum amount of the irradiation light of the light source to less than or equal to a first light amount by executing the power-saving control. The processor may be configured to temporarily set the maximum amount to a second light amount greater than the first light amount and temporarily set an amount of the irradiation light of the light source to a third light amount greater than the first light amount and less than or equal to the second light amount after a second period elapses from a time point of starting the power-saving control. The processor may be configured to compare first brightness with second brightness. The first brightness may be the brightness before the amount of the irradiation light of the light source becomes the third light amount. The second brightness may be the brightness when the amount of the irradiation light of the light source becomes the third light amount. The processor may be configured to determine whether or not the brightness meets a third condition. The third condition may represent that the second brightness is greater than the first brightness and the difference between the first brightness and the second brightness is greater than or equal to a third threshold value. The processor may be configured to determine that the imaging device has gone into the space when the brightness meets the third condition.

According to a fifth aspect of the present invention, an imaging apparatus includes a processor, an imaging device, a light source, and a lens of which a focal position is changeable. The processor is configured to determine whether or not the imaging device has gone out of space of which at least part is surrounded by an object when the imaging device is performing imaging after the imaging device is inserted into the space. The processor is configured to execute power-saving control when the processor determines that the imaging device has gone out of the space. In the power-saving control, the processor is configured to make power consumption of a control target less than power consumption of the control target before the power-saving control is executed. The control target is at least one of the imaging device and the light source. The processor is configured to adjust the focal position by executing autofocus control. The processor is configured to determine whether or not the focal position meets a fourth condition. The fourth condition represents that the focal position is continuously further than a first position in a fourth period and accuracy of the focal position is continuously low in the fourth period. The processor is configured to determine that the imaging device has gone out of the space when the focal position meets the fourth condition.

According to a sixth aspect of the present invention, in the fifth aspect, the processor may be configured to determine whether or not the focal position meets a fifth condition while the processor executes the power-saving control. The fifth condition represents that the focal position is continuously nearer than a second position in a fifth period or the accuracy is continuously high in the fifth period. The processor may be configured to determine that the imaging device has gone into the space when the focal position meets the fifth condition.

According to a seventh aspect of the present invention, an imaging apparatus includes a processor, an imaging device, and a light source. The processor is configured to determine whether or not the imaging device has gone out of space of which at least part is surrounded by an object when the imaging device is performing imaging after the imaging device is inserted into the space. The processor is configured to execute power-saving control when the processor determines that the imaging device has gone out of the space. In the power-saving control, the processor is configured to make power consumption of a control target less than power consumption of the control target before the power-saving control is executed. The control target is at least one of the imaging device and the light source. The object is a tubular wall surface. The processor is configured to estimate distance from the imaging device to the wall surface. The processor is configured to determine whether or not the distance meets a sixth condition. The sixth condition represents that the distance is continuously greater than a fourth threshold value in a sixth period. The processor is configured to determine that the imaging device has gone out of the space when the distance meets the sixth condition.

According to an eighth aspect of the present invention, in the seventh aspect, the processor may be configured to determine whether or not the distance meets a seventh condition while the processor executes the power-saving control. The seventh condition may represent that the distance is continuously less than a fifth threshold value in a seventh period. The processor may be configured to determine that the imaging device has gone into the space when the distance meets the seventh condition.

According to a ninth aspect of the present invention, in the first aspect, the imaging apparatus may further include a communicator. The control target may be at least one of the imaging device, the light source, and the communicator.

According to a tenth aspect of the present invention, a method of operating an imaging apparatus includes a first step and a second step. The imaging apparatus includes a processor, an imaging device configured to output image data, and a light source. The processor determines whether or not the imaging device has gone out of space of which at least part is surrounded by an object in the first step when the imaging device is performing imaging after the imaging device is inserted into the space. The processor executes power-saving control in the second step when the processor determines that the imaging device has gone out of the space. In the power-saving control, the processor is configured to make power consumption of a control target less than power consumption of the control target before the power-saving control is executed. The control target is at least one of the imaging device and the light source. The processor determines brightness on the basis of the image data. The processor reduces an amount of irradiation light of the light source when the brightness increases in a state in which the brightness is greater than or equal to a predetermined amount. The processor determines whether or not the brightness meets a first condition in the first step. The first condition represents that the brightness is continuously smaller than a first threshold value in a first period. The processor determines that the imaging device has gone out of the space in the first step when the brightness meets the first condition.

According to an eleventh aspect of the present invention, a non-transitory computer-readable recording medium saves a program for causing a processor of an imaging apparatus to execute a first step and a second step. The imaging apparatus includes a processor, an imaging device configured to output image data, and a light source. The processor determines whether or not the imaging device has gone out of space of which at least part is surrounded by an object in the first step when the imaging device is performing imaging after the imaging device is inserted into the space. The processor executes power-saving control in the second step when the processor determines that the imaging device has gone out of the space. In the power-saving control, the processor is configured to make power consumption of a control target less than power consumption of the control target before the power-saving control is executed. The control target is at least one of the imaging device and the light source. The processor determines brightness on the basis of the image data. The processor reduces an amount of irradiation light of the light source when the brightness increases in a state in which the brightness is greater than or equal to a predetermined amount. The processor determines whether or not the brightness meets a first condition in the first step. The first condition represents that the brightness is continuously smaller than a first threshold value in a first period. The processor determines that the imaging device has gone out of the space in the first step when the brightness meets the first condition.

DETAILED DESCRIPTION OF THE INVENTION

Hereinafter, embodiments of the present invention will be described with reference to the drawings.

First Embodiment

Figure 1:
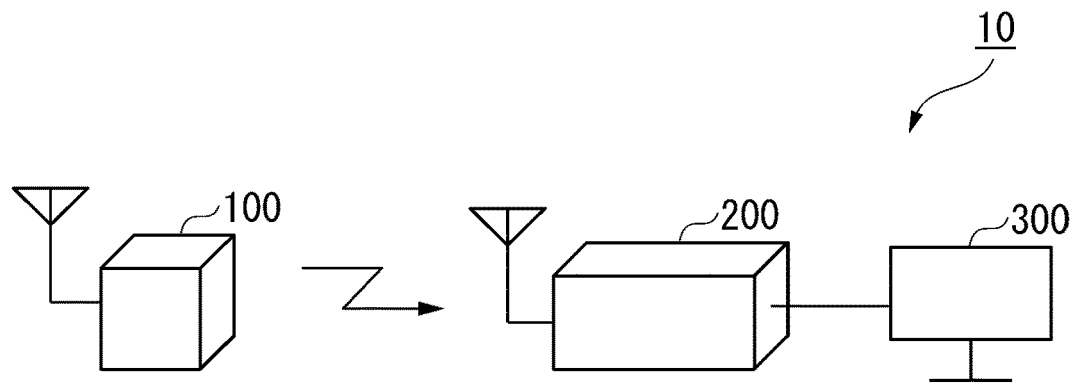
FIG. 1 is a block diagram showing a configuration of a wireless endoscope system according to a first embodiment of the present invention.

FIG. 1 shows a configuration of a wireless endoscope system 10 according to a first embodiment of the present invention. The wireless endoscope system 10 shown in FIG. 1 includes a transmission terminal 100, a reception terminal 200, and a monitor 300 (display). The transmission terminal 100 and the reception terminal 200 perform wireless communication. The reception terminal 200 is connected to the monitor 300 by a cable or the like. For example, the monitor 300 is constituted by a liquid crystal display device and a control circuit thereof. The reception terminal 200 and the monitor 300 may be integrated together.

Figure 2:
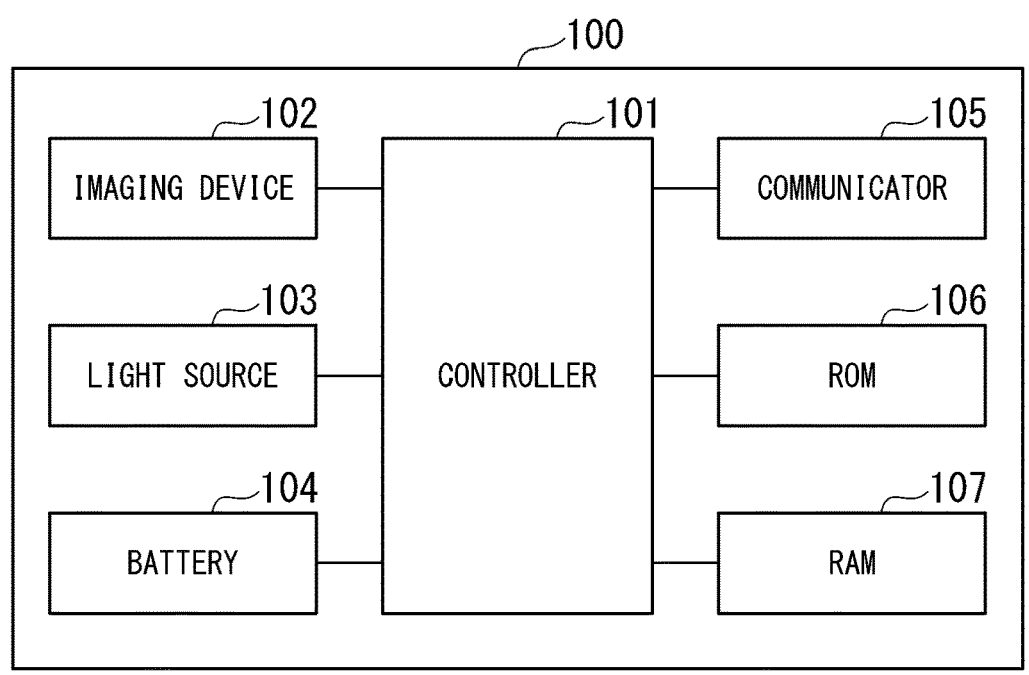
FIG. 2 is a block diagram showing a configuration of a transmission terminal according to the first embodiment of the present invention.

FIG. 2 shows a configuration of the transmission terminal 100. The transmission terminal 100 is an imaging apparatus. The transmission terminal 100 shown in FIG. 1 includes a controller 101, an imaging device 102, a light source 103, a battery 104, a communicator 105, a ROM 106, and a RAM 107.

When the imaging device 102 is performing imaging in space of which at least part is surrounded by an object, the controller 101 determines whether or not the imaging device 102 has gone out of the space. When the controller 101 determines that the imaging device 102 has gone out of the space, the controller 101 executes power-saving control. In the power-saving control, the controller 101 makes power consumption of a control target less than power consumption of the control target before the power-saving control is executed. The control target is at least one of the imaging device 102, the light source 103, and the communicator 105.

The imaging device 102 is to be inserted into an observation target including space. For example, the observation target is the nasal cavity, the oral cavity, the ear, the throat, the stomach, the duodenum, the gallbladder, the pancreas, the small intestine, the large intestine, the appendix, the anus, a blood vessel, the brain, a joint, a bone, the urethra, the bladder, the liver, the kidney, a genital organ, or the diaphragm. The observation target may be a portion in a human or animal body other than the above-described examples. In a case in which a plurality of portions are connected to each other, the space is the inside of any one of the plurality of portions and the outside of the space is the outside of the plurality of portions. The observation target is not limited to the portion in the body. The observation target may be an engine, a tubular pipe, a water pipe, or the like. For example, the entrance of the space and the exit of the space are the same. The imaging device 102 is inserted into the space through the entrance of the space. The imaging device 102 goes out of the space through the exit of the space. For example, an object surrounding the space is a tubular wall surface. The imaging device 102 images the object.

The control target may be any one of the imaging device 102, the light source 103, and the communicator 105. The control target may be any two of the imaging device 102, the light source 103, and the communicator 105. The control target may be all of the imaging device 102, the light source 103, and the communicator 105.

The controller 101 controls a power mode of the imaging device 102, the light source 103, and the communicator 105 on the basis of a result of the determination. The power mode is any one of a normal mode and the power-saving mode. In the normal mode, the transmission terminal 100 executes a normal function for observation. In the power-saving mode, the transmission terminal 100 does not execute the normal function and the electric power is reduced. In a case in which the controller 101 executes the power-saving control, the power mode becomes the power-saving mode.

The imaging device 102 is an image sensor (imager). For example, the imaging device 102 is a CCD or CMOS sensor. The imaging device 102 transforms light incident in the imaging device 102 into an electronic signal, that is, an imaging signal. The analog imaging signal is converted into a digital signal, that is, image data by analog-to-digital converter (AD converter). In other words, the imaging device 102 images a subject and generates the image data. The imaging device 102 images the subject in every imaging cycle and generates image data of each frame. The imaging device 102 outputs the image data to the controller 101.

For example, the light source 103 is a light-emitting diode (LED). The light source 103 generates illumination light. The light source 103 emits the illumination light to the space into which the transmission terminal 100 is to be inserted. The light source 103 illuminates the range imaged by the imaging device 102 by emitting the illumination light.

The battery 104 supplies power to the controller 101, the imaging device 102, the light source 103, the communicator 105, the ROM 106, and the RAM 107.

The communicator 105 (transmitter) is a wireless communicator. The communicator 105 includes an antenna. Alternatively, the communicator 105 is connected to the antenna. The communicator 105 performs wireless communication with the reception terminal 200. The communicator 105 transmits the image data to the reception terminal 200 by radio.

The ROM 106 is a nonvolatile memory such as a flash ROM. Program data and various pieces of setting information are stored on the ROM 106. The program data are used for controlling the transmission terminal 100. The setting information includes a communication setting parameter. The RAM 107 is a volatile memory. The RAM 107 is used as a buffer, a work area, and a temporary area. The buffer is used for temporarily storing image data. The work area is used for operations or the like executed by the controller 101. The temporary area is used for temporarily storing various pieces of setting information or the like.

While the normal mode is set to the transmission terminal 100, the controller 101 executes control for keeping constant the amount of light emitted to an object in the space. In a case in which the distance from the imaging device 102 to a subject is large, the controller 101 increases the amount of irradiation light of the light source 103. In a case in which the imaging device 102 goes out of the space, the subject is dark even when the amount of the irradiation light is increased. The controller 101 determines whether the imaging device 102 has gone out of the space by using this feature.

For example, in the power-saving control, the controller 101 may reduce the imaging rate of the imaging device 102, thereby making it less than the imaging rate in the normal mode. In the power-saving control, the controller 101 may reduce the resolution of image data generated by the imaging device 102, thereby making it less than the resolution in the normal mode. In the power-saving control, the controller 101 may reduce the amount of the irradiation light of the light source 103, thereby making it less than the amount of the irradiation light in the normal mode. In the power-saving control, the controller 101 may reduce the transmission rate of the communicator 105, thereby making it less than the transmission rate in the normal mode.

In the power-saving control, the controller 101 may turn off the power source of the control target. In this case, the controller 101 causes the battery 104 to stop supply of electric power to the control target. In the power-saving control, the controller 101 may turn off the power source of the entire transmission terminal 100. After the power source of the entire transmission terminal 100 is turned off, the transmission terminal 100 stops an operation until turning on the power source of the transmission terminal 100 is specified by a user.

The controller 101 outputs the image data output from the imaging device 102 to the communicator 105. The image data may be compressed. In the power-saving control, the controller 101 may reduce the compression rate of the image data, thereby making it less than the compression rate in the normal mode.

The controller 101 is constituted by at least one of a processor and a logic circuit. For example, the processor is at least one of a central processing unit (CPU), a digital signal processor (DSP), and a graphics processing unit (GPU). For example, the logic circuit is at least one of an application-specific integrated circuit (ASIC) and a field-programmable gate array (FPGA). The controller 101 may include one or a plurality of processors. The controller 101 may include one or a plurality of logic circuits. The controller 101 operates in accordance with a program stored on the ROM 106. In this way, the controller 101 controls the operations of the transmission terminal 100.

The controller 101 may read and execute a program. The program includes commands defining the operations of the controller 101. In other words, the functions of the controller 101 can be realized as software. This program, for example, may be provided by using a "computer-readable storage medium" such as a flash memory. The program may be transmitted from a computer storing the program to the transmission terminal 100 through a transmission medium or by using carrier waves in a transmission medium. The "transmission medium" transmitting a program is a medium that has a function of transmitting information. The medium that has a function of transmitting information includes a network (communication network) including the Internet and the like or a communication circuit line (communication line) including a telephone circuit line and the like. The program described above may realize at least some of the functions described above. Furthermore, the program described above may be a differential file (differential program). The functions described above may be realized by a combination of a differential program and a program that has already been recorded in a computer.

The controller 101 transmits the image data to the reception terminal 200 by using the communicator 105. Specifically, the controller 101 controls the communicator 105 such that the image data are transmitted to the reception terminal 200. In other words, the controller 101 causes the communicator 105 to transmit the image data for the reception terminal 200. In this way, the communicator 105 transmits the image data to the reception terminal 200.

Figure 3:
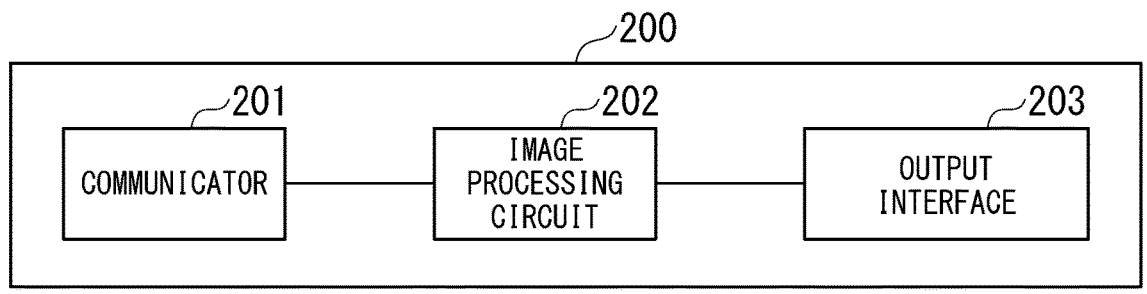
FIG. 3 is a block diagram showing a configuration of a reception terminal according to the first embodiment of the present invention.

FIG. 3 shows a configuration of the reception terminal 200. The reception terminal 200 shown in FIG. 3 includes a communicator 201, an image processing circuit 202, and an output interface 203.

The communicator 201 (receiver) is a wireless communicator. The communicator 201 includes an antenna. Alternatively, the communicator 201 is connected to the antenna. The communicator 201 performs wireless communication with the transmission terminal 100. The communicator 201 receives the image data from the transmission terminal 100 by radio. The communicator 201 outputs the received image data to the image processing circuit 202.

The image processing circuit 202 performs image processing on the image data received by the communicator 201. For example, the image processing circuit 202 converts the image data into display data in a format used for displaying an image. In a case in which the image data are compressed, the image processing circuit 202 may expand the image data. The image processing circuit 202 outputs the display data to the output interface 203.

The output interface 203 is connected to the monitor 300. The output interface 203 outputs the display data output from the image processing circuit 202 to the monitor 300. The monitor 300 displays an image on the basis of the display data.

The transmission terminal 100 and the reception terminal 200 may be connected together by a cable. In this case, the communicator 105 and the communicator 201 are connected together by the cable. The communicator 105 and the communicator 201 perform communication via the cable.

Figure 4:
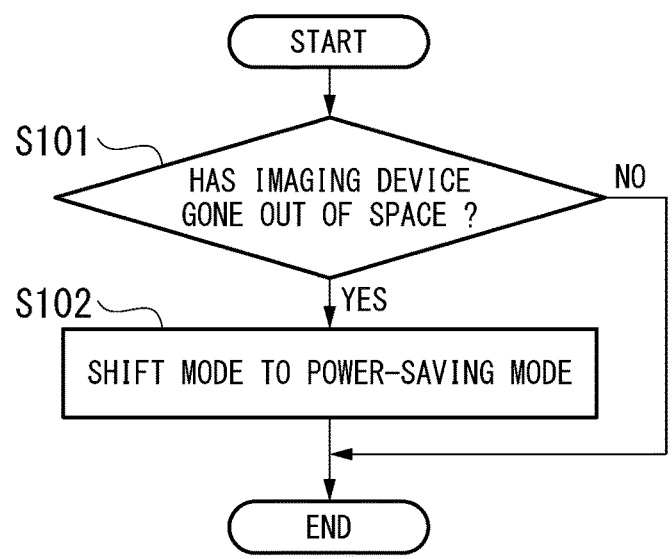
FIG. 4 is a flow chart showing a procedure of an operation of the transmission terminal according to the first embodiment of the present invention.

FIG. 4 shows a procedure of an operation of the transmission terminal 100 in the normal mode. The operation of the transmission terminal 100 will be described with reference to FIG. 4.

While the imaging device 102 is inserted into the space, the normal mode is set to the transmission terminal 100. While the normal mode is set to the transmission terminal 100, the imaging device 102 periodically images an object in the space. While the normal mode is set to the transmission terminal 100, the light source 103 generates illumination light and emits the illumination light to the object in the space. While the normal mode is set to the transmission terminal 100, the communicator 105 periodically transmits image data to the reception terminal 200.

The controller 101 determines whether or not the imaging device 102 has gone out of the space (Step S101). For example, the outside of the space is inside other space larger than the space into which the imaging device 102 is inserted. For example, the outside of the space is indoor space.

When the controller 101 determines that the imaging device 102 has gone out of the space in Step S101, the controller 101 executes the power-saving control (Step S102). In this way, the processing shown in FIG. 4 is completed. When the controller 101 determines that the imaging device 102 has not gone out of the space in Step S101, the processing shown in FIG. 4 is completed.

In Step S102, the controller 101 makes power consumption of a control target less than power consumption of the control target before the power-saving control is executed. The controller 101 changes the mode of the transmission terminal 100 from the normal mode to the power-saving mode in Step S102. Mode information that represents the power-saving mode is stored on the RAM 107.

An example of specific processing will be described. The imaging device 102 outputs image data. The controller 101 determines brightness on the basis of the image data. While the normal mode is set to the transmission terminal 100, determination of the brightness is continuously executed. When the brightness increases in a state in which the brightness is greater than or equal to a predetermined amount, the controller 101 reduces the amount of the irradiation light of the light source 103. For example, the controller 101 makes the brightness greater than or equal to the predetermined amount and also constant by controlling the amount of the irradiation light of the light source 103 on the basis of the image data. This control is executed independently of the processing shown in FIG. 4.

The controller 101 determines whether or not the brightness meets a brightness condition (first condition) in Step S101. The brightness condition represents that the brightness is continuously smaller than a brightness threshold value (first threshold value) in a determination period (first period). When the brightness meets the brightness condition, the controller 101 determines that the imaging device 102 has gone out of the space and executes the power-saving control in Step S102. When the brightness does not meet the brightness condition, the processing shown in FIG. 4 is completed.

The brightness threshold value may be the same as the above-described predetermined amount. The brightness threshold value may be different from the above-described predetermined amount. The brightness threshold value may be different between observation targets. For example, the brightness threshold value is experimentally decided on.

Figure 5:
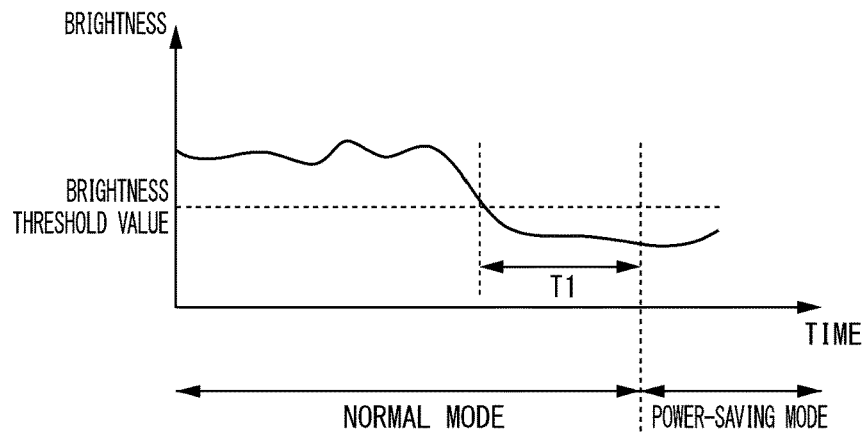
FIG. 5 is a graph showing the change in the brightness of an image in the first embodiment of the present invention.
Figure 6:
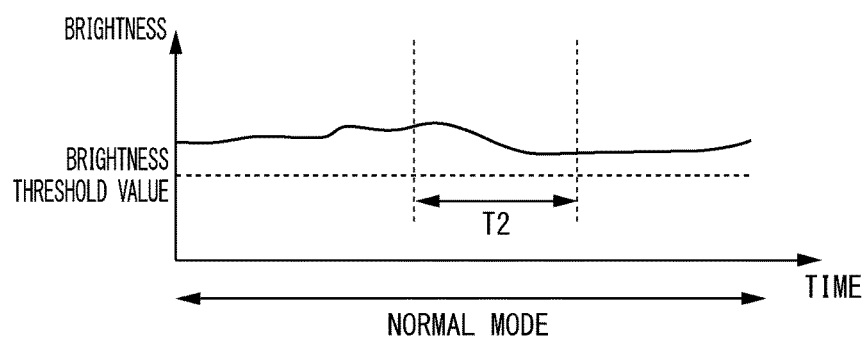
FIG. 6 is a graph showing the change in the brightness of an image in the first embodiment of the present invention.

FIG. 5 and FIG. 6 show the change in the brightness of an image. The horizontal axis of the graph shown in FIG. 5 and FIG. 6 represents time and the vertical axis of the graph shown in FIG. 5 and FIG. 6 represents the brightness.

The normal mode is set to the transmission terminal 100 and the controller 101 determines the brightness. For example, the brightness is an average value of all or some of the plurality of pixel values included in the image data. At all of the time points in a determination period T1 shown in FIG. 5, the brightness is less than the brightness threshold value. For this reason, the controller 101 determines that the brightness meets the brightness condition. At the time point at which the determination period T1 is completed, the controller 101 changes the mode of the transmission terminal 100 from the normal mode to the power-saving mode.

At all of the time points in a determination period T2 shown in FIG. 6, the brightness is greater than the brightness threshold value. For this reason, the controller 101 determines that the brightness does not meet the brightness condition. At the time point at which the determination period T2 is completed, the controller 101 maintains the mode of the transmission terminal 100 in the normal mode.

A method of operating an imaging apparatus according to each aspect of the present invention includes a first step (S101) and a second step (S102). A program according to each aspect of the present invention causes the controller 101 to execute the first step and the second step.

The range to which an imaging apparatus according to each aspect of the present invention is applied is not limited to a wireless endoscope system. As long as the imaging apparatus is inserted into the space and images an object inside the space, the range in which the imaging apparatus is used is not limited.

An imaging apparatus according to each aspect of the present invention does not need to include a communicator. Therefore, the transmission terminal 100 does not need to include the communicator 105. In such a case, a control target for the power-saving control is at least one of the imaging device 102 and the light source 103.

In the first embodiment, when the controller 101 determines that the imaging device 102 has gone out of the space, the controller 101 executes the power-saving control. For this reason, the transmission terminal 100 can reduce power consumption. It is unnecessary to load a new sensor for detecting the position of the imaging device 102 onto the transmission terminal 100.

Modified Example of First Embodiment

A modified example of the first embodiment of the present invention will be described. In the modified example of the first embodiment, the controller 101 determines whether or not the imaging device 102 has gone out of the space on the basis of the amount of the irradiation light of the light source 103.

The controller 101 determines the brightness on the basis of the image data. The controller 101 decides on the amount of the irradiation light of the light source 103 on the basis of the brightness. The controller 101 controls the light source 103 on the basis of the decided amount of the irradiation light.

The controller 101 determines whether or not the brightness meets a brightness condition in Step S101 shown in FIG. 4. The brightness condition represents that the amount of the irradiation light is continuously greater than a light amount threshold value in a determination period. When the amount of the irradiation light meets the brightness condition, the brightness is continuously less than the brightness threshold value in the first period. When the brightness meets the brightness condition, the controller 101 determines that the imaging device 102 has gone out of the space and executes the power-saving control in Step S102. The brightness threshold value may be different between observation targets. For example, the brightness threshold value is experimentally decided on.

Figure 7:
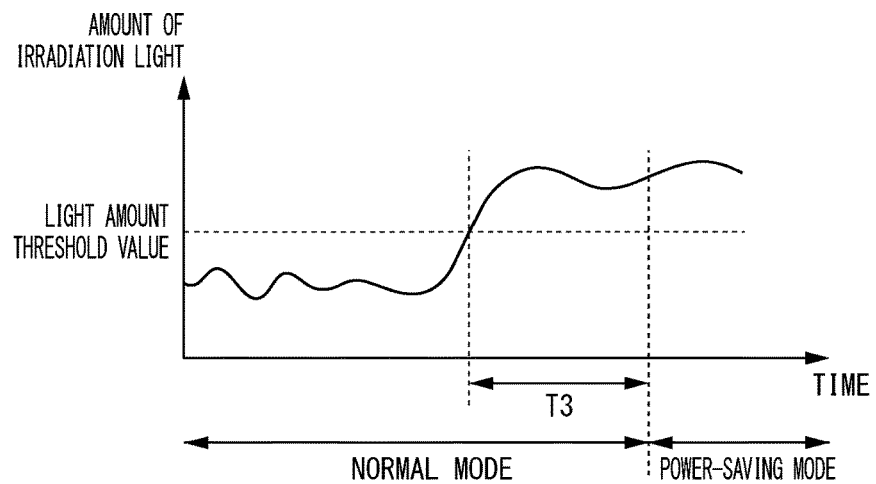
FIG. 7 is a graph showing the change in the amount of irradiation light of a light source in a modified example of the first embodiment of the present invention.
Figure 8:
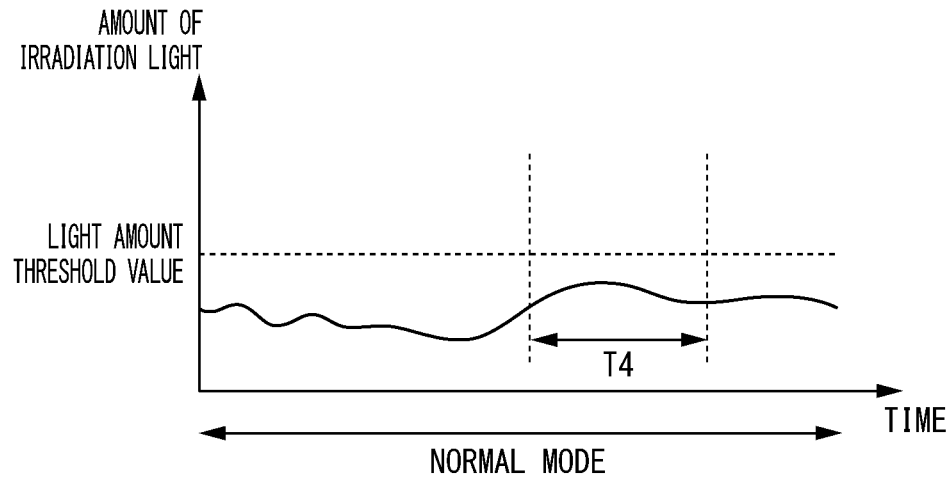
FIG. 8 is a graph showing the change in the amount of the irradiation light of the light source in the modified example of the first embodiment of the present invention.

FIG. 7 and FIG. 8 show the change in the amount of the irradiation light of the light source 103. The horizontal axis of the graph shown in FIG. 7 and FIG. 8 represents time and the vertical axis of the graph shown in FIG. 7 and FIG. 8 represents the amount of the irradiation light.

The normal mode is set to the transmission terminal 100 and the controller 101 determines the amount of the irradiation light. At all of the time points in a determination period T3 shown in FIG. 7, the amount of the irradiation light is greater than the light amount threshold value. For this reason, the controller 101 determines that the brightness meets the brightness condition. At the time point at which the determination period T3 is completed, the controller 101 changes the mode of the transmission terminal 100 from the normal mode to the power-saving mode.

At all of the time points in a determination period T4 shown in FIG. 8, the amount of the irradiation light is less than the light amount threshold value. For this reason, the controller 101 determines that the brightness does not meet the brightness condition. At the time point at which the determination period T4 is completed, the controller 101 maintains the mode of the transmission terminal 100 in the normal mode.

In a case in which the imaging device 102 has gone out of the space, a subject does not become bright even when the amount of the irradiation light increases. For this reason, the state in which the amount of the irradiation light is great continues. When the state in which the amount of the irradiation light is great continues, the controller 101 can determine that the imaging device 102 has gone out of the space.

Second Embodiment

Figure 9:
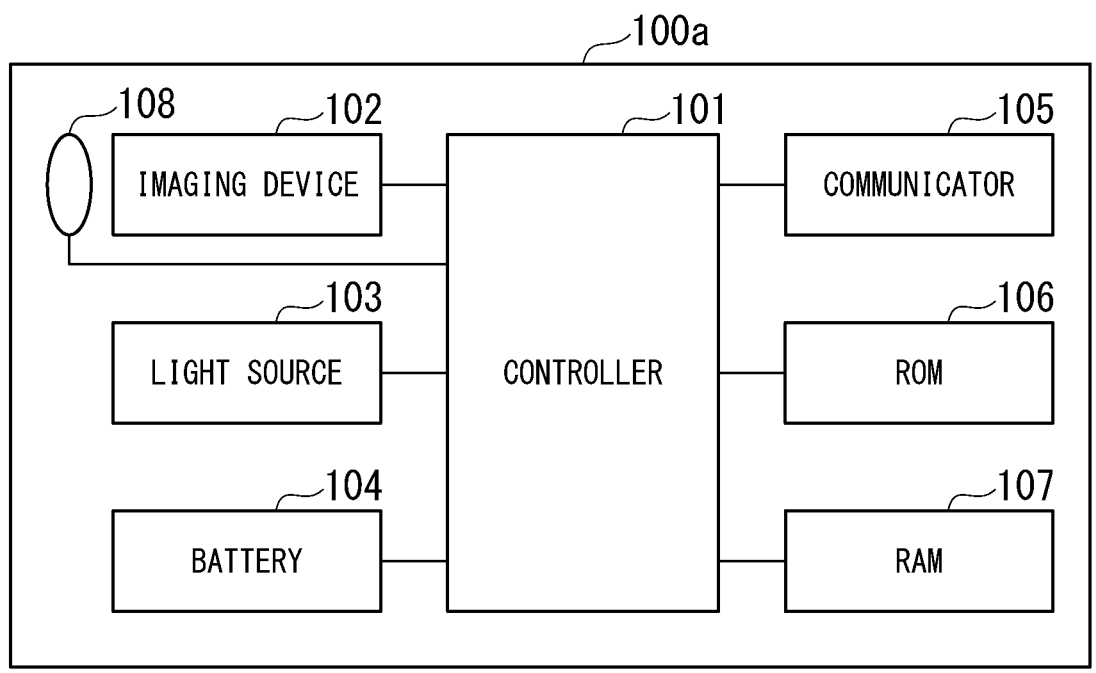
FIG. 9 is a block diagram showing a configuration of a transmission terminal according to a second embodiment of the present invention.

FIG. 9 shows a configuration of a transmission terminal 100a according to a second embodiment of the present invention. The same configuration as the configuration shown in FIG. 2 will not be described.

The transmission terminal 100a includes a lens 108 in addition to the configuration shown in FIG. 2. The lens 108 forms an optical image that is based on light reflected by a subject on the imaging device 102. The focal position of the lens 108 is changeable. The controller 101 executes auto-focus control (AF control).

The controller 101 adjusts depth of field by adjusting at least one of the focal position and the diaphragm. In this way, the controller 101 changes the imaging condition of the range to which light is emitted by the light source 103 to a condition suitable for imaging.

The transmission terminal 100a executes the processing shown in FIG. 4 in the normal mode. The same processing as the above-described processing will not be described.

The controller 101 adjusts the focal position by executing the auto-focus control. The auto-focus control is executed independently of the processing shown in FIG. 4. The controller 101 determines whether or not the focal position meets a focal condition (fourth condition) in Step S101. The focal condition represents that the focal position is continuously further than a predetermined position (first position) in a determination period (fourth period) and the accuracy of the focal position is continuously low in the determination period. In other words, the focal condition represents that the focal length is continuously longer than a predetermined length (first length) in the determination period and the accuracy of the focal position is continuously low in the determination period. When the predetermined position is between the lens 108 (or the imaging device 102) and the focal position, the focal position is further than the predetermined position. When the focal position is between the lens 108 (or the imaging device 102) and the predetermined position, the focal position is nearer than the predetermined position. When the focal position meets the focal condition, the controller 101 determines that the imaging device 102 has gone out of the space and executes the power-saving control in Step S102. When the focal position does not meet the focal condition, the processing shown in FIG. 4 is completed.

The predetermined position may be different between observation targets. The determination criterion of the accuracy of the focal position may be different between observation targets. For example, the predetermined position and the determination criterion of the accuracy of the focal position are experimentally decided on.

Figure 10:
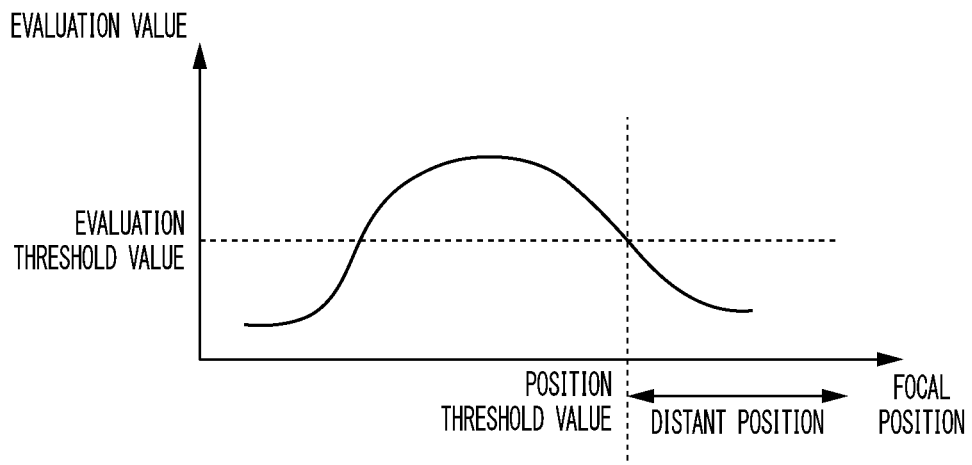
FIG. 10 is a graph showing the relationship between a focal position and an evaluation value in the second embodiment of the present invention.

FIG. 10 shows the relationship between the focal position and an evaluation value. The horizontal axis of the graph shown in FIG. 10 represents the focal position and the vertical axis of the graph shown in FIG. 10 represents the evaluation value.

The controller 101 calculates the evaluation value (AF evaluation value) on the basis of the image data in the auto-focus control. For example, the evaluation value is a contrast value. The controller 101 causes the focal position of the lens 108 to continuously change from a first position to a second position. The second position is located further than the first position. Alternatively, the second position is located nearer than the first position. The controller 101 calculates the evaluation value for each of a plurality of focal positions. The plurality of focal positions are located in the range from the first position to the second position. The controller 101 decides on a focal position at which the evaluation value is the greatest. The controller 101 sets the focal position of the lens 108 to the focal position that has been decided on.

The controller 101 compares the focal position with a position threshold value. The focal position to be compared with the position threshold value is the focal position that has been decided on in the auto-focus control. When the focal position is greater than the position threshold value, the controller 101 determines that the focal position is further than the predetermined position.

The controller 101 compares the evaluation value with an evaluation threshold value. The evaluation value to be compared with the evaluation threshold value is an evaluation value corresponding to the focal position that has been decided on in the auto-focus control. When the evaluation value is less than the evaluation threshold value, the controller 101 determines that the accuracy of the focal position is low.

When the focal position is continuously greater than the position threshold value in the determination period and the evaluation value is continuously less than the evaluation threshold value in the determination period, the controller 101 determines that the focal position meets the focal condition. Otherwise, the controller 101 determines that the focal position does not meet the focal condition.

In a case in which the imaging device 102 has gone out of the space, the focal position becomes distant and the focal position is not fixed. In a case in which such a state continues, the controller 101 can determine that the imaging device 102 has gone out of the space.

The auto-focus is a function mounted on most imaging apparatuses. The controller 101 determines the position of the imaging device 102 on the basis of the focal position. For this reason, the increase of power consumption of the transmission terminal 100a is restricted regarding the determination of the position of the imaging device 102.

Third Embodiment

A third embodiment of the present invention will be described by using the transmission terminal 100 shown in FIG. 2. In the third embodiment, the controller 101 determines whether or not the imaging device 102 has gone out of the space on the basis of the distance from the imaging device 102 to an object in the space.

The transmission terminal 100 executes the processing shown in FIG. 4 in the normal mode. The same processing as the above-described processing will not be described.

The object in the space is a tubular wall surface. The controller 101 estimates the distance from the imaging device 102 to the wall surface in Step S101. The controller 101 determines whether or not the distance meets a distance condition (sixth condition) in Step S101. The distance condition represents that the distance is continuously greater than a distance threshold value (fourth threshold value) in a determination period (sixth period). When the distance meets the distance condition, the controller 101 determines that the imaging device 102 has gone out of the space and executes the power-saving control in Step S102. When the distance does not meet the distance condition, the processing shown in FIG. 4 is completed. The distance threshold value may be different between observation targets. For example, the distance threshold value is experimentally decided on.

Figure 11:
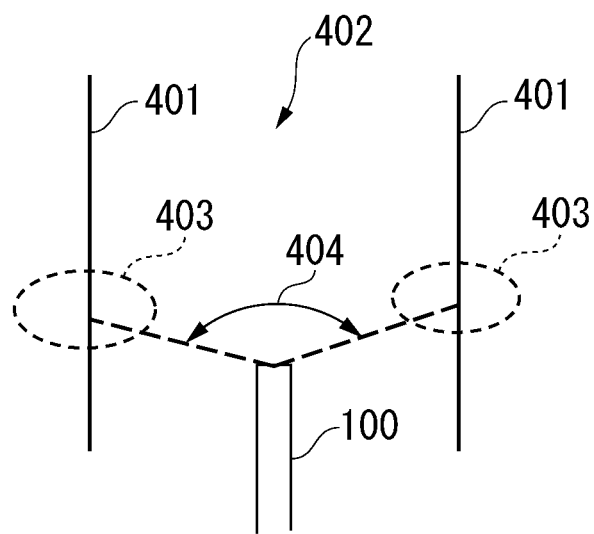
FIG. 11 is a diagram showing a method of estimating distance in a third embodiment of the present invention.

FIG. 11 shows a method of estimating the distance from the imaging device 102 to a wall surface 401. The transmission terminal 100 is positioned in a space 402 surrounded by the wall surface 401. The controller 101 estimates the distance from the imaging device 102 to the wall surface 401 on the basis of the image data. The controller 101 uses the data of an edge part 403 of the image acquired by the imaging device 102. The edge part 403 is positioned at the outer edge of an imaging range 404 of the imaging device 102.

For example, the controller 101 detects the brightness of the edge part 403 of the image and the hue of the edge part 403 of the image on the basis of the image data. When the imaging device 102 is positioned close to the wall surface 401, light reflected by a subject is strong and the image is bright. When the imaging device 102 is positioned far from the wall surface 401, the light reflected by the subject is weak and the image is dark. The hue of the image represents a pixel value of each color, the smoothness of change in color, or the like. For example, the controller 101 performs pattern matching related to the brightness and the hue. Specifically, the controller 101 collates the brightness of the edge part 403 of the image with the brightness of a reference image. The controller 101 collates the hue of the edge part 403 of the image with the hue of the reference image. The reference image is an image of a reference subject and is prepared for each distance to the reference subject.

The controller 101 estimates the distance from the imaging device 102 to the wall surface 401 on the basis of the result of the pattern matching. Specifically, the controller 101 selects a reference image for which the matching degree with the edge part 403 of the image is high regarding the brightness and the hue. The distance associated with the selected reference image is an estimation result.

In a case in which the transmission terminal 100 includes an optical system used for measurement, the controller 101 may estimate the distance from the imaging device 102 to the wall surface 401 on the basis of the image data by using the principle of stereo measurement or the like.

In a case in which the imaging device 102 has gone out of the space, the distance from the imaging device 102 to the wall surface 401 becomes large. In a case in which such a state continues, the controller 101 can determine that the imaging device 102 has gone out of the space.

The controller 101 estimates the distance from the imaging device 102 to the wall surface 401 on the basis of the image data. The controller 101 determines the position of the imaging device 102 on the basis of the estimated distance. For this reason, the increase of power consumption of the transmission terminal 100 is restricted regarding the determination of the position of the imaging device 102.

Fourth Embodiment

A fourth embodiment of the present invention will be described by using the transmission terminal 100 shown in FIG. 2. In the fourth embodiment, the controller 101 determines whether or not to return from the operation in the power-saving mode to the operation in the normal mode.

Figure 12:
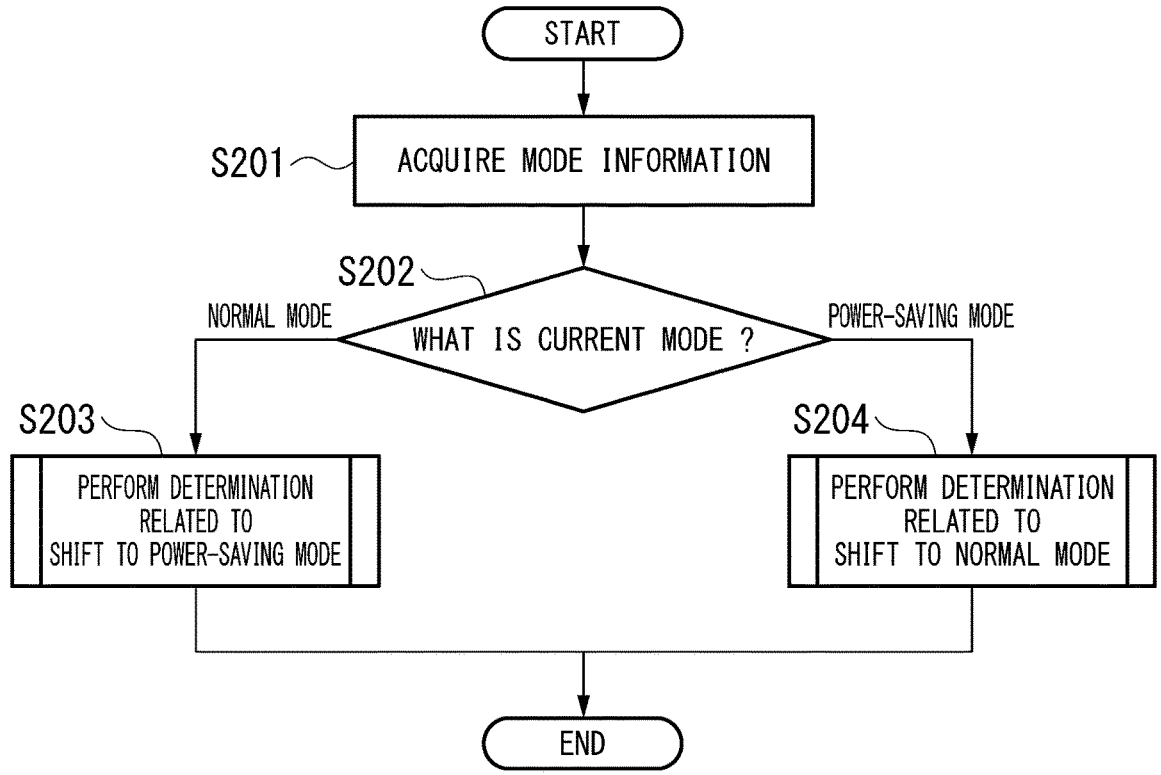
FIG. 12 is a flow chart showing a procedure of an operation of a transmission terminal according to a fourth embodiment of the present invention.

FIG. 12 shows a procedure of an operation of the transmission terminal 100. The operation of the transmission terminal 100 will be described with reference to FIG. 12.

The controller 101 acquires mode information from the RAM 107 (Step S201). The mode information represents the mode of the transmission terminal 100. The mode of the transmission terminal 100 is set to any one of the normal mode and the power-saving mode. When the transmission terminal 100 is activated, either the normal mode or the transmission mode may be set to the transmission terminal 100.

After Step S201, the controller 101 determines the current mode of the transmission terminal 100 on the basis of the mode information (Step S202).

When the controller 101 determines that the current mode of the transmission terminal 100 is the normal mode in Step S202, the processing in Step S203 is executed. The processing in Step S203 includes determination related to a shift to the power-saving mode. The transmission terminal 100 executes the processing shown in FIG. 4 in Step S203. In Step S203, the processing described in any one of the first to third embodiments is executed.

When the controller 101 determines that the current mode of the transmission terminal 100 is the power-saving mode in Step S202, the processing in Step S204 is executed. The processing in Step S204 includes determination related to a shift to the normal mode.

When the processing in Step S203 or Step S204 is executed, the processing shown in FIG. 12 is completed. The processing shown in FIG. 12 may be repeatedly executed.

Figure 13:
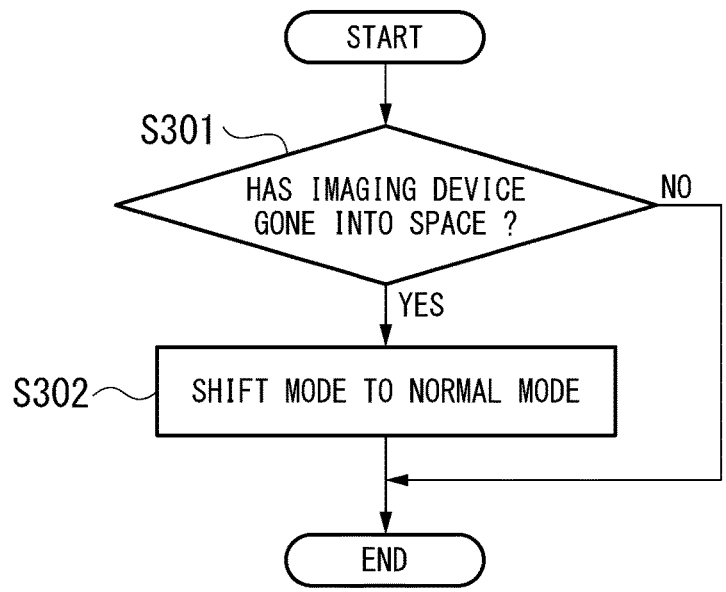
FIG. 13 is a flow chart showing a procedure of an operation of the transmission terminal according to the fourth embodiment of the present invention.

FIG. 13 shows the processing in Step S204. The operation of the transmission terminal 100 will be described with reference to FIG. 13.

While the controller 101 executes the power-saving control, the controller 101 determines whether or not the imaging device 102 has gone into the space (Step S301). When the controller 101 determines that the imaging device 102 has gone into the space in Step S301, the controller 101 stops the power-saving control (Step S302). When the controller 101 determines that the imaging device 102 has not gone into the space in Step S301, the processing shown in FIG. 13 is completed.

In Step S302, the controller 101 makes power consumption of a control target greater than power consumption of the control target when the imaging device 102 is positioned outside the space. The controller 101 changes the mode of the transmission terminal 100 from the power-saving mode to the normal mode in Step S302. Mode information that represents the normal mode is stored on the RAM 107.

For example, the controller 101 may increase the imaging rate of the imaging device 102 in Step S302, thereby making it greater than the imaging rate in the power-saving mode. The controller 101 may increase the resolution of image data generated by the imaging device 102 in Step S302, thereby making it greater than the resolution in the power-saving mode. The controller 101 may increase the amount of the irradiation light of the light source 103 in Step S302, thereby making it greater than the amount of the irradiation light in the power-saving mode. The controller 101 may increase the transmission rate of the communicator 105 in Step S302, thereby making it greater than the transmission rate in the power-saving mode.

When the communicator 105 is turned off in Step S102 shown in FIG. 4, the controller 101 may turn on the power source of the communicator 105 in Step S302. The controller 101 causes the battery 104 to start supply of electric power to the communicator 105 in order to turn on the power source of the communicator 105.

Returning the mode of the transmission terminal 100 to the normal mode immediately after the mode of the transmission terminal 100 is shifted from the normal mode to the power-saving mode may be avoided. For example, the processing in Step S301 may be executed after a certain amount of time has elapsed from the time point of shifting the mode of the transmission terminal 100 from the normal mode to the power-saving mode.

An example of specific processing will be described. The imaging device 102 outputs image data. The controller 101 determines brightness on the basis of the image data. While the power-saving mode is set to the transmission terminal 100, determination of the brightness is continuously executed. The controller 101 controls the amount of the irradiation light of the light source 103 on the basis of the brightness. When the brightness increases in a state in which the brightness is greater than or equal to a predetermined amount, the controller 101 reduces the amount of the irradiation light of the light source 103. For example, the controller 101 makes the brightness greater than or equal to the predetermined amount and also constant by controlling the amount of the irradiation light of the light source 103 on the basis of the image data. This control is executed independently of the processing shown in FIG. 13.

The controller 101 restricts the maximum amount of the irradiation light of the light source 103 to less than or equal to a predetermined light amount (first light amount) by executing the power-saving control in Step S102. After a predetermined period (second period) elapses from the time point of starting the power-saving control, the controller 101 temporarily sets the maximum amount of the irradiation light of the light source 103 to a predetermined light amount (second light amount) in Step S301. The second light amount is greater than the first light amount. While the maximum amount of the irradiation light of the light source 103 is temporarily set to the second light amount, the controller 101 determines whether or not the brightness meets a brightness condition (second condition) in Step S301. The brightness condition represents that the brightness is continuously greater than a brightness threshold value (second threshold value) in a determination period (third period). When the brightness meets the brightness condition, the controller 101 determines that the imaging device 102 has gone into the space and stops the power-saving control in Step S302. When the brightness does not meet the brightness condition, the processing shown in FIG. 13 is completed. In this case, the controller 101 continues the power-saving control.

When the brightness does not meet the brightness condition, the controller 101 restricts the maximum amount of the irradiation light of the light source 103 to less than or equal to the predetermined light amount (first light amount) again.

The maximum amount of the irradiation light is the maximum value of the amount of light that the light source 103 is allowed to emit. For example, the controller 101 calculates the amount of the irradiation light of the light source 103 on the basis of the image data in order to make the brightness greater than or equal to a predetermined amount and also constant. The controller 101 sets the calculated amount of the irradiation light to the light source 103. When the calculated amount of the irradiation light exceeds the maximum amount of the irradiation light, the controller 101 sets the maximum amount of the irradiation light to the light source 103.

The brightness threshold value (second threshold value) in the fourth embodiment may be the same as the brightness threshold value (first threshold value) in the first embodiment. The brightness threshold value (second threshold value) in the fourth embodiment may be different from the brightness threshold value (first threshold value) in the first embodiment. The brightness threshold value may be the same as the above-described predetermined amount. The brightness threshold value may be different from the above-described predetermined amount. The length of the determination period (third period) in Step S301 may be the same as the length of the determination period (first period) in Step S101. The length of the third period may be different from the length of the first period.

Figure 14:
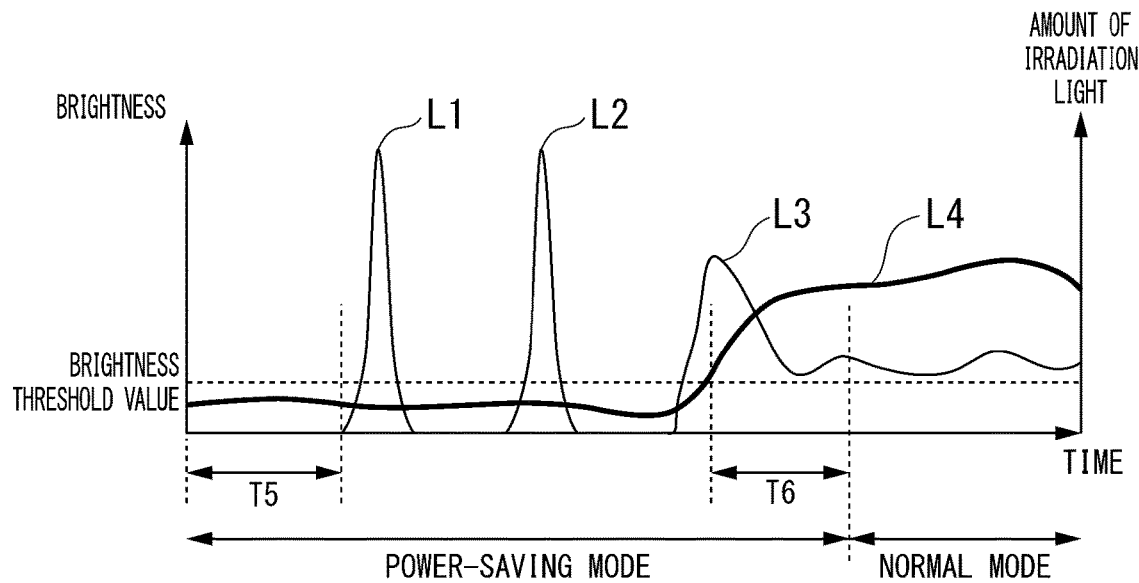
FIG. 14 is a graph showing the change in the brightness of an image and the change in the amount of irradiation light of a light source in the fourth embodiment of the present invention.
Figure 15:
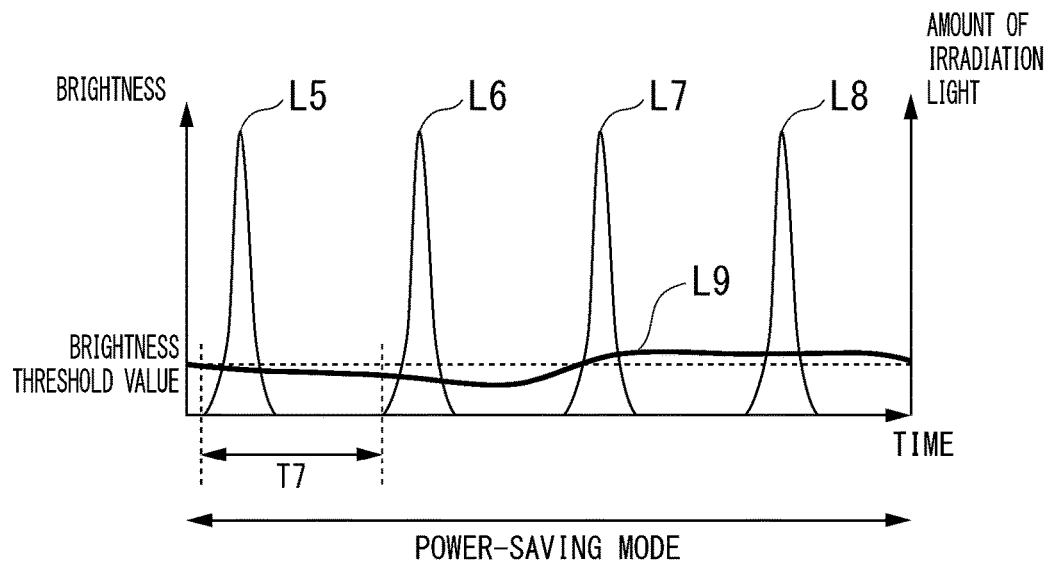
FIG. 15 is a graph showing the change in the brightness of an image and the change in the amount of the irradiation light of the light source in the fourth embodiment of the present invention.

FIG. 14 and FIG. 15 show the change in the brightness of an image and the change in the amount of the irradiation light of the light source 103. The horizontal axis of the graph shown in FIG. 14 and FIG. 15 represents time and the vertical axis of the graph shown in FIG. 14 and FIG. 15 represents the brightness and the amount of the irradiation light. A line L1, a line L2, a line L3, a line L5, a line L6, a line L7, and a line L8 represent the amount of the irradiation light. A line L4 and a line L9 represent the brightness.

An example shown in FIG. 14 will be described. After a period T5 elapses from the time point of starting the power-saving control, the controller 101 sets the maximum amount of the irradiation light of the light source 103 to the second light amount. In this way, the controller 101 releases the restriction to the maximum amount of the irradiation light of the light source 103. Since the imaging device 102 is out of the space, the image is dark. While the amount of the irradiation light of the light source 103 represented by the line L1 increases, the brightness represented by the line L4 does not change very much. Since the change in the brightness is less than a predetermined amount, the controller 101 restricts the maximum amount of the irradiation light of the light source 103 again. The controller 101 periodically releases the restriction to the maximum amount of the irradiation light of the light source 103.

The imaging device 102 goes into the space. The controller 101 restricts the maximum amount of the irradiation light of the light source 103 again. When the amount of the irradiation light of the light source 103 represented by the line L3 increases, the brightness represented by the line L4 increases. Since the brightness continues to increase, the controller 101 decreases the amount of the irradiation light of the light source 103 represented by the line L3.

The controller 101 determines the brightness. At all of the time points in a determination period T6, the brightness is greater than the brightness threshold value. For this reason, the controller 101 determines that the brightness meets the brightness condition. At the time point at which the determination period T6 is completed, the controller 101 changes the mode of the transmission terminal 100 from the power-saving mode to the normal mode.

An example shown in FIG. 15 will be described. At all of the time points in a determination period T7, the brightness is less than the brightness threshold value. For this reason, the controller 101 determines that the brightness does not meet the brightness condition. At the time point at which the determination period T7 is completed, the controller 101 maintains the mode of the transmission terminal 100 in the power-saving mode.

In the fourth embodiment, when the controller 101 determines that the imaging device 102 has gone into the space, the controller 101 stops the power-saving control. For this reason, the transmission terminal 100 can execute a normal operation. It is not necessary to mount a new sensor in the transmission terminal 100 in order to detect the position of the imaging device 102.

Modified Example of Fourth Embodiment

A modified example of the fourth embodiment of the present invention will be described. In the modified example of the fourth embodiment, the controller 101 determines the amount of change in brightness.

The imaging device 102 outputs image data. The controller 101 determines brightness on the basis of the image data. While the power-saving mode is set to the transmission terminal 100, determination of the brightness is continuously executed. The controller 101 controls the amount of the irradiation light of the light source 103 on the basis of the brightness. When the brightness increases in a state in which the brightness is greater than or equal to a predetermined amount, the controller 101 reduces the amount of the irradiation light of the light source 103. For example, the controller 101 makes the brightness greater than or equal to the predetermined amount and also constant by controlling the amount of the irradiation light of the light source 103 on the basis of the image data.

The controller 101 restricts the maximum amount of the irradiation light of the light source 103 to less than or equal to a predetermined light amount (first light amount) by executing the power-saving control in Step S102. After a predetermined period (second period) elapses from the time point of starting the power-saving control, the controller 101 temporarily sets the maximum amount of the irradiation light of the light source 103 to a predetermined light amount (second light amount) and temporarily sets the amount of the irradiation light of the light source 103 to a predetermined light amount (third light amount) in Step S301. The second light amount is greater than the first light amount. The third light amount is greater than the first light amount and is less than or equal to the second light amount.

The controller 101 compares first brightness with second brightness in Step S301. The first brightness is the brightness before the amount of the irradiation light of the light source 103 becomes the third light amount in Step S301. The second brightness is the brightness when the amount of the irradiation light of the light source 103 becomes the third light amount in Step S301. The controller 101 determines whether or not the brightness meets a brightness condition (third condition). The brightness condition represents that the second brightness is greater than the first brightness and the difference between the first brightness and the second brightness is greater than or equal to a brightness threshold value (third threshold value). When the brightness meets the brightness condition, the controller 101 determines that the imaging device 102 has gone into the space and stops the power-saving control in Step S302. When the brightness does not meet the brightness condition, the processing shown in FIG. 13 is completed. In this case, the controller 101 continues the power-saving control.

When the brightness does not meet the brightness condition, the controller 101 restricts the maximum amount of the irradiation light of the light source 103 to less than or equal to the predetermined light amount (first light amount) again.

The amount of the irradiation light of the light source 103 may be set to the maximum amount of the irradiation light in Step S301. Alternatively, the amount of the irradiation light of the light source 103 may be set to an amount that is based on the maximum amount of the irradiation light in Step S301. For example, the amount is in a predetermined ratio (90% or the like) to the maximum amount of the irradiation light.

The brightness threshold value (third threshold value) in the modified example of the fourth embodiment may be the same as the brightness threshold value (first threshold value) in the first embodiment. The brightness threshold value (third threshold value) in the modified example of the fourth embodiment may be different from the brightness threshold value (first threshold value) in the first embodiment. The brightness threshold value may be the same as the above-described predetermined amount. The brightness threshold value may be different from the above-described predetermined amount.

Figure 16:
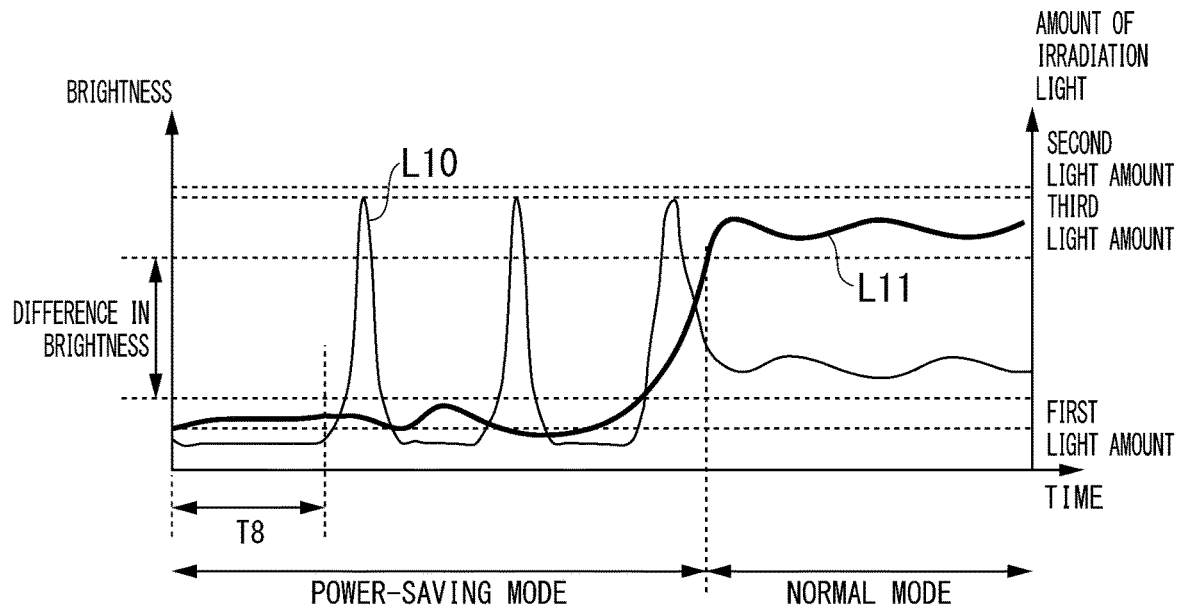
FIG. 16 is a graph showing the change in the brightness of an image and the change in the amount of irradiation light of a light source in a modified example of the fourth embodiment of the present invention.
Figure 17:
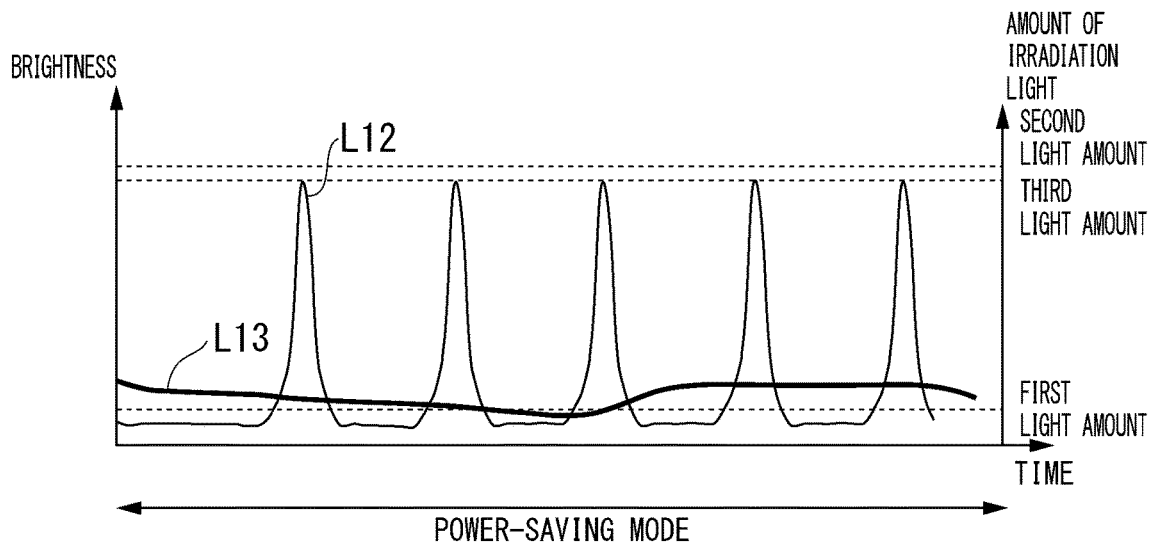
FIG. 17 is a graph showing the change in the brightness of an image and the change in the amount of the irradiation light of the light source in the modified example of the fourth embodiment of the present invention.

FIG. 16 and FIG. 17 show the change in the brightness of an image and the change in the amount of the irradiation light of the light source 103. The horizontal axis of the graph shown in FIG. 16 and FIG. 17 represents time and the vertical axis of the graph shown in FIG. 16 and FIG. 17 represents the brightness and the amount of the irradiation light. A line L10 and a line L12 represent the amount of the irradiation light. A line L11 and a line L13 represent the brightness.

An example shown in FIG. 16 will be described. After a period T8 elapses from the time point of starting the power-saving control, the controller 101 sets the maximum amount of the irradiation light of the light source 103 to the second light amount. In this way, the controller 101 releases the restriction to the maximum amount of the irradiation light of the light source 103. In addition, the controller 101 sets the amount of the irradiation light of the light source 103 to the third light amount. Since the imaging device 102 is out of the space, the image is dark. While the amount of the irradiation light of the light source 103 represented by the line L10 increases, the brightness represented by the line L11 does not change very much. Since the change in the brightness is less than a predetermined amount, the controller 101 restricts the maximum amount of the irradiation light of the light source 103 again. The controller 101 periodically releases the restriction to the maximum amount of the irradiation light of the light source 103 and sets the amount of the irradiation light of the light source 103 to the third light amount.

The imaging device 102 goes into the space. The controller 101 releases the restriction to the maximum amount of the irradiation light of the light source 103 again and sets the amount of the irradiation light of the light source 103 to the third light amount. When the amount of the irradiation light of the light source 103 represented by the line L10 increases, the brightness represented by the line L11 increases. Since the brightness continues to increase, the controller 101 decreases the amount of the irradiation light of the light source 103 represented by the line L10.

The controller 101 compares the first brightness before the amount of the irradiation light of the light source 103 increases with the second brightness after the amount of the irradiation light of the light source 103 increases. The controller 101 calculates the difference between the first brightness and the second brightness. Since the difference is greater than the brightness threshold value, the controller 101 determines that the brightness meets the brightness condition. At this time, the controller 101 changes the mode of the transmission terminal 100 from the power-saving mode to the normal mode.

An example shown in FIG. 17 will be described. The controller 101 periodically releases the restriction to the maximum amount of the irradiation light of the light source 103 and sets the amount of the irradiation light of the light source 103 to the third light amount. While the amount of the irradiation light of the light source 103 represented by the line L12 increases, the brightness represented by the line L13 does not change very much. For this reason, the controller 101 determines that the brightness does not meet the brightness condition. The controller 101 maintains the mode of the transmission terminal 100 in the power-saving mode.

When the imaging device 102 goes into the space, a subject becomes bright in accordance with the increase in the amount of the irradiation light. For this reason, the change in the brightness becomes large. When the change in the brightness becomes large, the controller 101 can determine that the imaging device 102 has gone into the space.

Fifth Embodiment

A fifth embodiment of the present invention will be described by using the transmission terminal 100a shown in FIG. 9. In the fifth embodiment, the controller 101 determines whether or not to return from the operation in the power-saving mode to the operation in the normal mode on the basis of the focal position.

The transmission terminal 100a executes the processing shown in FIG. 12. The transmission terminal 100a executes the processing shown in FIG. 4 in Step S203. In Step S203, the processing described in any one of the first to third embodiments is executed. The transmission terminal 100a executes the processing shown in FIG. 13 in Step S204. The same processing as the above-described processing will not be described.

The controller 101 adjusts the focal position by executing the auto-focus control. The auto-focus control is executed independently of the processing shown in FIG. 13. While the controller 101 executes the power-saving control, the controller 101 determines whether or not the focal position meets a focal condition (fifth condition) in Step S301. The focal condition represents that the focal position is continuously nearer than a predetermined position (second position) in a determination period (fifth period) or the accuracy of the focal position is continuously high in a focal period. In other words, the focal condition represents that the focal length is continuously shorter than a predetermined length (second length) in the determination period or the accuracy of the focal position is continuously high in the focal period. When the focal position is between the lens 108 (or the imaging device 102) and the predetermined position, the focal position is nearer than the predetermined position. When the predetermined position is between the lens 108 (or the imaging device 102) and the focal position, the focal position is further than the predetermined position. When the focal position meets the focal condition, the controller 101 determines that the imaging device 102 has gone into the space and stops the power-saving control in Step S302. When the focal position does not meet the focal condition, the processing shown in FIG. 13 is completed. In this case, the controller 101 continues the power-saving control.

The focal condition includes two conditions. One of the two conditions is that the focal position is continuously nearer than the predetermined position (second position) in the determination period (fifth period). The other of the two conditions is that the accuracy of the focal position is continuously high in the focal period. When the focal position meets only any one of the two conditions or the focal position meets the two conditions, the controller 101 stops the power-saving control.

The predetermined position may be different between observation targets. The determination criterion of the accuracy of the focal position may be different between observation targets. For example, the predetermined position and the determination criterion of the accuracy of the focal position are experimentally decided on.

The predetermined position (second position) to be compared with the focal position in Step S301 may be the same as the predetermined position (first position) to be compared with the focal position in Step S101. The second position may be different from the first position. The length of the determination period (fifth period) in Step S301 may be the same as the length of the determination period (fourth period) in Step S101. The length of the fifth period may be different from the length of the fourth period.

The controller 101 calculates an evaluation value (AF evaluation value) on the basis of the image data in the auto-focus control. The controller 101 compares the focal position with a position threshold value (see FIG. 10). The focal position to be compared with the position threshold value is the focal position that has been decided on in the auto-focus control. When the focal position is less than the position threshold value, the controller 101 determines that the focal position is nearer than the predetermined position.

The controller 101 compares the evaluation value with an evaluation threshold value (see FIG. 10). The evaluation value to be compared with the evaluation threshold value is an evaluation value corresponding to the focal position that has been decided on in the auto-focus control. When the evaluation value is greater than the evaluation threshold value, the controller 101 determines that the accuracy of the focal position is high.

When the focal position is continuously less than the position threshold value in the determination period or the evaluation value is continuously greater than the evaluation threshold value in the determination period, the controller 101 determines that the focal position meets the focal condition. Otherwise, the controller 101 determines that the focal position does not meet the focal condition.

In a case in which the imaging device 102 has gone into the space, the focal position becomes near or the focal position is fixed. In a case in which such a state continues, the controller 101 can determine that the imaging device 102 has gone into the space.

The auto-focus is a function mounted on most imaging apparatuses. The controller 101 determines the position of the imaging device 102 on the basis of the focal position. For this reason, the increase of power consumption of the transmission terminal 100a is restricted regarding the determination of the position of the imaging device 102.

Sixth Embodiment

A sixth embodiment of the present invention will be described by using the transmission terminal 100 shown in FIG. 2. In the sixth embodiment, the controller 101 determines whether or not to return from the operation in the power-saving mode to the operation in the normal mode on the basis of the distance from the imaging device 102 to a tubular wall surface.

The transmission terminal 100 executes the processing shown in FIG. 12. The transmission terminal 100 executes the processing shown in FIG. 4 in Step S203. In Step S203, the processing described in any one of the first to third embodiments is executed. The transmission terminal 100 executes the processing shown in FIG. 13 in Step S204. The same processing as the above-described processing will not be described.

The controller 101 estimates the distance from the imaging device 102 to the wall surface in Step S301. The method of estimating the distance is the same as the method described in the third embodiment. While the controller 101 executes the power-saving control, the controller 101 determines whether or not the distance meets a distance condition (seventh condition). The distance condition represents that the distance is continuously less than a distance threshold value (fifth threshold value) in a determination period (seventh period). When the distance meets the distance condition, the controller 101 determines that the imaging device 102 has gone into the space and stops the power-saving control in Step S302. When the distance does not meet the distance condition, the processing shown in FIG. 13 is completed. In this case, the controller 101 continues the power-saving control. The distance threshold value may be different between observation targets. For example, the distance threshold value is experimentally decided on.

The distance threshold value (fifth threshold value) to be referred to in Step S301 may be the same as the distance threshold value (fourth threshold value) to be referred to in Step S101. The fifth threshold value may be different from the fourth threshold value. The length of the determination period (seventh period) in Step S301 may be the same as the length of the determination period (fourth period) in Step S101. The length of the seventh period may be different from the length of the fourth period.

In a case in which the imaging device 102 has gone into the space, the distance from the imaging device 102 to the wall surface becomes near. In a case in which such a state continues, the controller 101 can determine that the imaging device 102 has gone into the space.

The controller 101 estimates the distance from the imaging device 102 to the wall surface on the basis of the image data. The controller 101 determines the position of the imaging device 102 on the basis of the estimated distance. For this reason, the increase of power consumption of the transmission terminal 100 is restricted regarding the determination of the position of the imaging device 102.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging apparatus comprising:
a processor;
an imaging device configured to output image data; and
a light source,
wherein the processor is configured to determine whether or not the imaging device has gone out of space of which at least part is surrounded by an object when the imaging device is performing imaging after the imaging device is inserted into the space,
the processor is configured to execute power-saving control when the processor determines that the imaging device has gone out of the space,
in the power-saving control, the processor is configured to make power consumption of a control target less than power consumption of the control target before the power-saving control is executed,
the control target is at least one of the imaging device and the light source,
the processor is configured to determine brightness on the basis of the image data,
the processor is configured to reduce an amount of irradiation light of the light source when the brightness increases in a state in which the brightness is greater than or equal to a predetermined amount,
the processor is configured to determine whether or not the brightness meets a first condition,
the first condition represents that the brightness is continuously smaller than a first threshold value in a first period, and
the processor is configured to determine that the imaging device has gone out of the space when the brightness meets the first condition.

2. The imaging apparatus according to claim 1,
wherein the processor is configured to determine whether or not the imaging device has gone into the space while the processor executes the power-saving control, and
the processor is configured to stop the power-saving control when the processor determines that the imaging device has gone into the space.

3. The imaging apparatus according to claim 2,
wherein the processor is configured to restrict the maximum amount of the irradiation light of the light source to less than or equal to a first light amount by executing the power-saving control,
the processor is configured to temporarily set the maximum amount to a second light amount greater than the first light amount after a second period elapses from a time point of starting the power-saving control,
the processor is configured to determine whether or not the brightness meets a second condition while the maximum amount is temporarily set to the second light amount,
the second condition represents that the brightness is continuously greater than a second threshold value in a third period, and
the processor is configured to determine that the imaging device has gone into the space when the brightness meets the second condition.

4. The imaging apparatus according to claim 2,
wherein the processor is configured to restrict the maximum amount of the irradiation light of the light source to less than or equal to a first light amount by executing the power-saving control,
the processor is configured to temporarily set the maximum amount to a second light amount greater than the first light amount and temporarily set an amount of the irradiation light of the light source to a third light amount greater than the first light amount and less than or equal to the second light amount after a second period elapses from a time point of starting the power-saving control,
the processor is configured to compare first brightness with second brightness,
the first brightness is the brightness before the amount of the irradiation light of the light source becomes the third light amount,
the second brightness is the brightness when the amount of the irradiation light of the light source becomes the third light amount,
the processor is configured to determine whether or not the brightness meets a third condition, the third condition represents that the second brightness is greater than the first brightness and the difference between the first brightness and the second brightness is greater than or equal to a third threshold value, and the processor is configured to determine that the imaging device has gone into the space when the brightness meets the third condition.

5. An imaging apparatus comprising:

a processor;

an imaging device;

a light source; and a lens of which a focal position is changeable, wherein the processor is configured to determine whether or not the imaging device has gone out of space of which at least part is surrounded by an object when the imaging device is performing imaging after the imaging device is inserted into the space, the processor is configured to execute power-saving control when the processor determines that the imaging device has gone out of the space, in the power-saving control, the processor is configured to make power consumption of a control target less than power consumption of the control target before the power-saving control is executed, the control target is at least one of the imaging device and the light source, the processor is configured to adjust the focal position by executing auto-focus control, the processor is configured to determine whether or not the focal position meets a fourth condition, the fourth condition represents that the focal position is continuously further than a first position in a fourth period and accuracy of the focal position is continuously low in the fourth period, and the processor is configured to determine that the imaging device has gone out of the space when the focal position meets the fourth condition.

6. The imaging apparatus according to claim 5, wherein the processor is configured to determine whether or not the focal position meets a fifth condition while the processor executes the power-saving control, the fifth condition represents that the focal position is continuously nearer than a second position in a fifth period or the accuracy is continuously high in the fifth period, and the processor is configured to determine that the imaging device has gone into the space when the focal position meets the fifth condition.

7. An imaging apparatus comprising:

a processor;

an imaging device; and a light source, wherein the processor is configured to determine whether or not the imaging device has gone out of space of which at least part is surrounded by an object when the imaging device is performing imaging after the imaging device is inserted into the space, the processor is configured to execute power-saving control when the processor determines that the imaging device has gone out of the space, in the power-saving control, the processor is configured to make power consumption of a control target less than power consumption of the control target before the power-saving control is executed, the control target is at least one of the imaging device and the light source, the object is a tubular wall surface, the processor is configured to estimate distance from the imaging device to the wall surface, the processor is configured to determine whether or not the distance meets a sixth condition, the sixth condition represents that the distance is continuously greater than a fourth threshold value in a sixth period, and the processor is configured to determine that the imaging device has gone out of the space when the distance meets the sixth condition.

8. The imaging apparatus according to claim 7, wherein the processor is configured to determine whether or not the distance meets a seventh condition while the processor executes the power-saving control, the seventh condition represents that the distance is continuously less than a fifth threshold value in a seventh period, and the processor is configured to determine that the imaging device has gone into the space when the distance meets the seventh condition.

9. The imaging apparatus according to claim 1, further comprising a communicator, wherein the control target is at least one of the imaging device, the light source, and the communicator.

10. A method of operating an imaging apparatus, the method comprising a first step and a second step, wherein the imaging apparatus includes a processor, an imaging device configured to output image data, and a light source, the processor determines whether or not the imaging device has gone out of space of which at least part is surrounded by an object in the first step when the imaging device is performing imaging after the imaging device is inserted into the space, the processor executes power-saving control in the second step when the processor determines that the imaging device has gone out of the space, in the power-saving control, the processor is configured to make power consumption of a control target less than power consumption of the control target before the power-saving control is executed, the control target is at least one of the imaging device and the light source, the processor determines brightness on the basis of the image data, the processor reduces an amount of irradiation light of the light source when the brightness increases in a state in which the brightness is greater than or equal to a predetermined amount, the processor determines whether or not the brightness meets a first condition in the first step, the first condition represents that the brightness is continuously smaller than a first threshold value in a first period, and the processor determines that the imaging device has gone out of the space in the first step when the brightness meets the first condition.

11. A non-transitory computer-readable recording medium saving a program for causing a processor of an imaging apparatus to execute a first step and a second step,
wherein the imaging apparatus includes
the processor,
an imaging device configured to output image data, and
a light source,
the processor determines whether or not the imaging device has gone out of space of which at least part is surrounded by an object in the first step when the imaging device is performing imaging after the imaging device is inserted into the space,
the processor executes power-saving control in the second step when the processor determines that the imaging device has gone out of the space,
in the power-saving control, the processor is configured to make power consumption of a control target less than power consumption of the control target before the power-saving control is executed,
the control target is at least one of the imaging device and the light source,
the processor determines brightness on the basis of the image data,
the processor reduces an amount of irradiation light of the light source when the brightness increases in a state in which the brightness is greater than or equal to a predetermined amount,
the processor determines whether or not the brightness meets a first condition in the first step,
the first condition represents that the brightness is continuously smaller than a first threshold value in a first period, and
the processor determines that the imaging device has gone out of the space in the first step when the brightness meets the first condition.

* * * * *